(12) United States Patent
Liu

(10) Patent No.: US 8,621,915 B2
(45) Date of Patent: Jan. 7, 2014

(54) APPARATUS AND METHODS FOR MULTIDIMENSIONAL ANALYSIS

(75) Inventor: Hongji Liu, Grafton, MA (US)

(73) Assignee: Waters Technologies Corp., Milford, MA (US)

( * ) Notice: Subject to any disclaimer, the term of this patent is extended or adjusted under 35 U.S.C. 154(b) by 535 days.

(21) Appl. No.: 12/601,035

(22) PCT Filed: May 27, 2008
(Under 37 CFR 1.47)

(86) PCT No.: PCT/US2008/064858
§ 371 (c)(1),
(2), (4) Date: Oct. 11, 2010

(87) PCT Pub. No.: WO2008/150763
PCT Pub. Date: Dec. 11, 2008

(65) Prior Publication Data
US 2011/0247403 A1    Oct. 13, 2011

Related U.S. Application Data

(60) Provisional application No. 60/940,469, filed on May 29, 2007.

(51) Int. Cl.
*G01N 30/02*    (2006.01)
(52) U.S. Cl.
USPC ......... 73/61.55; 73/61.56; 210/656; 210/659; 422/70; 436/161
(58) Field of Classification Search
USPC ..................... 73/61.52, 61.53, 61.55, 61.56; 210/198.2; 436/161
See application file for complete search history.

(56) References Cited

U.S. PATENT DOCUMENTS

| | | | | |
|---|---|---|---|---|
| 5,389,221 A * | 2/1995 | Jorgenson et al. | ............ | 204/603 |
| 6,802,967 B2 * | 10/2004 | Masuda et al. | ............ | 210/198.2 |
| 6,864,099 B2 * | 3/2005 | Regnier | ........................ | 436/174 |
| 6,942,793 B2 * | 9/2005 | Ito et al. | ..................... | 210/198.2 |
| 7,214,313 B2 * | 5/2007 | Hayashi et al. | ............ | 210/198.2 |
| 7,537,694 B2 * | 5/2009 | Watanabe et al. | .......... | 210/198.2 |
| 8,101,422 B2 * | 1/2012 | Srinivasan et al. | ............ | 436/161 |
| 2004/0072375 A1 * | 4/2004 | Gjerde et al. | ................. | 436/541 |
| 2005/0218055 A1 * | 10/2005 | Hayashi et al. | ............ | 210/198.2 |

(Continued)

FOREIGN PATENT DOCUMENTS

WO    2006078859    7/2006

OTHER PUBLICATIONS

Cadapakam J. Venkatramani and Yury Zelechonok, "An Automated Orthogonal Two-Dimensional Liquid Chromatograph" Journal of Analytical Chemistry, v. 75, pp. 3484-3494 (2003).*

(Continued)

*Primary Examiner* — Leonard Chang
*Assistant Examiner* — Natalie Huls
(74) *Attorney, Agent, or Firm* — Waters Technologies Corporation

(57) ABSTRACT

The invention provides improved methods and apparatus for multidimensional analysis, especially for multidimensional liquid chromatography. Methods and apparatus for the quantitative determination of one or more components comprised in a sample mixture are described. Methods and apparatus of the invention typically allow accurate quantitative determination of more components of the mixture than prior multidimensional methods. The invention is particularly useful for, but is not limited to the analysis of complex mixtures of peptides and proteins.

35 Claims, 4 Drawing Sheets

(56) References Cited

U.S. PATENT DOCUMENTS

| | | | |
|---|---|---|---|
| 2006/0156792 A1* | 7/2006 | Wang | 73/23.37 |
| 2006/0219638 A1* | 10/2006 | Watanabe et al. | 210/656 |
| 2007/0199874 A1* | 8/2007 | Ito et al. | 210/198.2 |
| 2007/0295062 A1* | 12/2007 | Wang | 73/61.55 |
| 2009/0126466 A1* | 5/2009 | Gilar et al. | 73/61.55 |
| 2010/0107742 A1* | 5/2010 | Liu et al. | 73/61.56 |
| 2010/0218585 A1* | 9/2010 | Chawla et al. | 73/1.02 |
| 2011/0030457 A1* | 2/2011 | Valery et al. | 73/61.53 |
| 2011/0097813 A1* | 4/2011 | Ito et al. | 436/161 |
| 2012/0240666 A1* | 9/2012 | Sims | 73/61.56 |

OTHER PUBLICATIONS

Mayr, et al; "Absolute Myoglobin Quantiation in Serum by Combining Two-Dimensional Liquid Chromatography-Electrospray ionization Mass Spectrometry and Novel Data Analysis Algorithms" J. Proteome Research 2006, vol. 5 pp. 414-421.

Allen, et al; "Isolation of the components of a complex misture by means of column switching for their enhanced detection by mass spectrometry", Journal of Chromatography A, 913 (2001) pp. 209-219.

Pascoe, et al; Reduce in Matrix-Related Signal Suppression Effects in Electrospray Ionization Mass Spectrometry Using On-Line Two-Dimensional Liquid Chromatography, Anal Chem 2001, 73, pp. 6014-6023.

Bushey, et al; Automated Instrumentaion for Comprehensive Two-Dimensional High-Performance Liquid Crhomatography of Proteins, Anal. Chem 1990, vol. 62, pp. 161-167.

Rose, et al; "Two-Dimensional Gel Electrophoresis/Liquid Chromatography for the Micropreparative Isolation of Proteins", Anal. Chem. 1994, vol. 66, pp. 2529-2536.

Venkatramani, et al; "An Automated Orthogonal Two-Dimensional Liquid Chromatography", Anal. Chem. 2003, vol. 75, pp. 3484-3494.

Murphy, et al; "Effect of Sampling Rate on Resolution in Comprehensive Two-Dimensional Liquid Chromatography", Anal. Chem. 1998, 70, pp. 1585-1594.

Shelfon, Edward M.; "Development of a LC-LC-MS complete heart-cut approach for the characterizaiton of pharmaceutical comppounds using standard instrumentation", Journal of Pharmaceutical and Biomedical Analysis, vol. 31, 2003, pp. 1153-1166.

Gu, et al; "Large-bore particle-entrapped monolithic precolumns prepared by a sol-gel method for on-line peptides trapping and preconcentration in multidimensional liquid chromatography system for proteome analysis", Journal of Chromatography A, 1072 (2005) pp. 223-232.

Gray, et al; "Utilising retention correlation for the separation of oligostyrenes by coupled-column liquid chromatography", Journal of Chromatography A, 1073 (2005) pp. 3-9.

Zheng, et al; "Determination of urinary nucleosides by direct injection and coupled-column high-performance liquid chromatography", Journal of Chromatography B, 819 (2005), pp. 85-90.

\* cited by examiner

APPARATUS AND METHODS FOR MULTIDIMENSIONAL ANALYSIS

CROSS REFERENCE TO RELATED APPLICATIONS

This application claims benefit of and is a continuation of International Application No. PCT/US08/064858, filed on May 27, 2008 and designating the United States, which claims benefit of a priority from U.S. Provisional Patent Application No. 60/940,469, filed on May 29, 2007.

STATEMENT ON FEDERALLY SPONSORED RESEARCH

N/A

FIELD OF INVENTION

This invention relates to improved methods and apparatus for multidimensional analysis, and especially to apparatus involving multi-dimensional liquid chromatography and liquid chromatography-mass spectrometry. The invention further provides multidimensional apparatus and methods for the quantitative determination of one or more components comprised in a sample mixture using improved methods of calibration. Apparatus and methods according to the invention are particularly useful for, but not limited to, the analysis of complicated mixtures of peptides and proteins.

BACKGROUND TO THE INVENTION

Multidimensional analysis methods and apparatus are especially suitable for use with complex biochemical samples. An example of such multidimensional apparatus comprises two chromatographic columns in series, wherein the two columns are typically selected to cause separation of the components according to different physiochemical properties. For example, the first dimension column may be such as to separate components by ion pair chromatography while the second dimension column may be a reverse-phase analytical column. In such a system, components eluting from the first dimension column pass directly into the second dimension column where they are subjected to further separation before arriving at a detector.

Although most commonly used with liquid mobile phases and especially for HPLC, multidimensional chromatographic systems for gas chromatography or supercritical fluid chromatography, or combinations of all three, are known.
A limitation of the simple system wherein two or more columns are simply connected in series is that the same mobile phase must pass through both columns. Further, especially in the case of samples comprising many components, there is a danger that once a first batch of components has passed through the first dimension column and is undergoing separation of the second dimension column, some components comprised in a second batch eluting from the first dimension column may pass onto the second dimension column and interfere with the separation thereon of the first batch of components.

These problems can be overcome by interposing one or more traps between the first and second dimension columns. This allows the temporary storage of a second batch of components eluting from the first dimension column while a first batch is undergoing separation on the second dimension column. It also allows the use of different mobile phases for the first and second dimension separations. For example, by means of a suitable arrangement of valves, a first mobile phase may be employed to carry out a first dimension separation and to trap a batch of components, and a second mobile phase may be used to release the trapped components and to carry out a second dimension separation. In some cases, when the first mobile phase is such that it does not cause components to be eluted from the second dimension column, it may be possible to dispense with a separate trap and to trap batches of components at the head of the second dimension column before changing the mobile phase to one which will elute the trapped components.

Where provided, a suitable trap may comprise a short chromatographic column capable of trapping at least some of the components entering it in the mobile phase used for the first dimension separation. In some cases it may comprise a chromatographic absorbent similar to that used in the second dimension column, but other types of trap may also be used, for example traps based on affinity or immunological binding. Trapped components may be released from the trap when required by introduction of a different, stronger, mobile phase.

When a trap is provided downstream of the first dimension column, the second dimension column may be replaced by alternative analytical apparatus, for example a mass spectrometer. Using such apparatus, a typical method of analysis may comprise trapping at least some of the components as they elute from the first dimension column and subsequently releasing batches of them into the mass spectrometer for further analysis.

Quantitative calibration of multidimensional analysis systems is more difficult than it is for single dimension systems. For example, an internal standard added to a complex sample analysed on a multidimensional system will typically elute in only one or a few of the batches of sample components which elute from the first dimension column, and therefore can only provide a reference for those batches as they undergo further separation on the second dimension column (or analysis in analytical apparatus such as a mass spectrometer). Unfortunately, it is often impractical to overcome this difficulty by providing many different internal standards, each appropriate for the components of each batch eluting from the first dimension. Consequently, in the past, quantitative calibration of multidimensional chromatographic systems has often been carried out merely by separately running one or more samples comprising a known amount of a component whose concentration in a complex mixture is to be determined, using identical chromatographic conditions. The quantity of the component in the complex mixture may then be determined by comparing the heights or areas of the relevant chromatographic peaks obtained from the calibration sample and the mixture. Such a method is of course less accurate than calibration using an internal standard added to the sample itself because it relies on the chromatographic conditions being identical for the run of the calibration sample and the run of the mixture. In practice, in view of the long time periods typically required for multidimensional chromatography, and the complexity of the methods used, maintaining the conditions sufficiently similar for accurate quantification is very difficult. Other errors may also arise if the matrix in which the calibration sample is comprised is significantly different from that in which the sample is comprised. Use of a mass spectrometer to detect compounds eluting from the chromatographic system, commonplace when complex samples are being analysed, adds further to these quantification problems because its sensitivity can be affected by many other factors that may also vary with time and matrix composition.

Similar difficulties in quantification arise in systems where the second dimension column is omitted and eluent from the trap is fed directly to a mass spectrometer.

There is therefore a need for multidimensional analysis apparatus and methods in which the problems associated with quantitative calibration are minimized. It is an object of the present invention to provide such apparatus and methods. It is another object of the invention to provide methods and apparatus for quantitative multidimensional analysis that do not require internal standards to be added to a complex sample. It is further object to provide methods and apparatus for quantitative multidimensional analysis that do not rely on comparing chromatographic parameters obtained during different runs.

According to a first aspect, an embodiment of the invention provides a method of chromatography comprising the following steps:

First, a sample comprising one or more sample components is introduced into a first mobile phase, and the resulting solution is passed through first chromatographic media so that at least some of the sample components are retained on the first chromatographic media. Then, a releasing phase comprising calibration material is passed through the first chromatographic media. The releasing phase is such as to cause at least some of the sample components previously retained on the first chromatographic media to be released from that media into the releasing phase. The calibration material is such that it is not retained on the first chromatographic media in the presence of the releasing phase and may comprise one or more chemical species. The releasing phase comprising the released sample components and the calibration material is passed into second chromatographic media which is capable of separating at least some of the released sample components and the calibration material. The eluent from the second chromatographic media is passed into detector means. The detector means generates signals indicative of the amount of at least some of the sample components and the calibration material present in the eluent. These signals are then processed to yield quantitative information about at least some of the sample components relative to the calibration material.

In some embodiments, only some of the sample components retained on the first chromatographic media are released by the passage of the releasing phase. Once further separation of the released sample components on the second chromatographic media is completed (or sufficiently advanced to ensure there will be no interference), a second batch of sample components may be released from the first chromatographic media by passing another releasing phase into it. This releasing phase may also comprise calibration material, and will typically be stronger than the releasing phase originally used so that a second batch of sample components, more strongly retained on the first chromatographic media, may be released. The releasing phase comprising the second batch of sample components and the calibration material may then be passed into the second chromatographic media and at least some of the sample components therein may be quantitatively determined in the same way as described for the first batch of sample components.

A convenient way of generating different releasing phases is to provide a plurality of reservoirs, each containing a releasing agent as well as the calibration material. Each reservoir may contain a different concentration of releasing agent. The contents of a reservoir may be introduced into the flow of first mobile phase to generate a releasing phase as required. This may be done using the same apparatus provided for introducing a sample into the flow of first mobile phase, for example a sample valve and sample loop similar to those conventionally used in liquid chromatography. For example, if the first chromatographic separation media comprises a strong cation exchange media, the releasing agent may comprise salt solutions having different concentrations in different reservoirs.

The process may be repeated using still stronger releasing phases, each capable of releasing another batch of sample components retained on the first chromatographic media, and each releasing phase comprising calibration material that is not retained on the first chromatographic media. In this way calibration material will elute in every batch of sample components transmitted to the second chromatographic media, allowing quantitative calibration of the sample components. This overcomes the problem inherent in prior multidimensional methods wherein the calibration material elutes only with certain batches of sample components.

In a variation, the releasing phases may be modified by the addition of a modifying phase as they exit from the first chromatographic media, thereby generating a second mobile phase that passes to the second chromatographic media. The modifying phase may be selected so that the resultant second mobile phase is more suitable for carrying out the separation on the second chromatographic media than the releasing phases alone. The composition of the modifying phase may be varied with time, permitting gradient elution to be carried out. The flow of releasing phase may be discontinued once the sample components have all passed onto the second chromatographic media so that the additional solvent provides the sole source of mobile phase for the second chromatographic media. A splitting device may also be provided so that only a portion of the releasing phase and/or the modifying phase passes to the second chromatographic media.

It will be appreciated that in the above methods each of the releasing phases used to release sample components from the first chromatographic media enters the second chromatographic media and comprises at least a part of the second mobile phase used to carry out the separations on that media, at least for some of the time during which a separation is being carried out. In certain cases this may degrade the separation, or even be substantially incompatible with it, even if the releasing phase is modified as described. The invention therefore provides methods of quantitative multidimensional analysis having more general applicability. In these methods, batches of sample components released from the first chromatographic media are trapped on trapping media before being passed to a second analysis device. This may comprise a second chromatographic column or an analyzer such as a mass spectrometer. Thus the first mobile phase and/or releasing phases may be used to carry sample components from the first chromatographic media to trapping media rather than directly to the second chromatographic media or analyzer. The trapping media should be capable of trapping thereon at least some of the sample components in the presence of the first mobile phase or releasing phases eluting from the first chromatographic media. During this stage of the methods, the first mobile phase and/or releasing phases may be diverted to waste rather than being passed to the second separation media or analytical device. When a batch of sample components has been trapped on the trapping media, the flow of first mobile phase or releasing phase may be discontinued and a separate supply of a second mobile phase may be used to release at least some of them from the trapping media, to pass them to the second separation means or analytical device. Another separation may then be carried out on the second separation media, or an analysis carried out on the analytical device.

The trapping media may be comprised in a separate chromatographic column, and may have properties similar to those of the second chromatographic media where provided. Alternatively, the trapping media may comprise part of the second chromatographic media itself, so that sample components are trapped on the initial portion of the second chromatographic media itself, until the second mobile phase is introduced. This variation requires that the first mobile phase and releasing phases pass through the second chromatographic media and may not always be applicable.

In all cases, however, calibration material is provided in each of the releasing phases. The calibration material, which may comprise one or more chemical species, may be selected so that in the presence of the releasing phase it is either not retained or is only retained for a short time on the first chromatographic media, but is capable of being trapped on the trapping media along with the sample components. Calibration material may then be released by the second mobile phase and may pass with the sample components into the second chromatographic media or analysis device, thereby allowing at least relative quantitative determination of at least some of the sample components in that batch.

The use of intermediate trapping between the first chromatographic media and second chromatographic media or analysis device decouples the first and second dimension separation from the second dimension separation or analysis. This may allow a conventional chromatographic separation to be carried out on the first chromatographic media, in place of the trapping and subsequent batch releasing of sample components described above. In such a case, unresolved groups of sample components eluting from the first chromatographic media may be trapped on the trapping media, and subsequently released by a second mobile phase to pass into the analysis device or second chromatographic media where they may undergo further separation. An aliquot of calibration material may be separately introduced into the first mobile phase. The calibration material, which may comprise one or more chemical species, should not be retained, or be retained only for a short time, on the first chromatographic media, but should be retained on the trapping media along with the sample components. Alternatively, calibration material may be introduced into the second mobile phase.

Calibration material may be introduced into a mobile phase or a releasing phase by means of a sample valve configured to introduce a fixed volume of a solution comprising the calibration material into the flow of the phase. Alternatively, in embodiments where a fixed volume of releasing phase is used to release a batch of trapped sample components, each releasing phase may comprise calibration material. When a fixed volume of the releasing phase is injected into a mobile phase that in the absence of the releasing solvent is incapable of releasing any sample components from the chromatographic or trapping media, this method will introduce a fixed quantity of the calibration material. Typically, several different releasing phases of different strengths are prepared, each containing the calibration material. These different strength phases may then be introduced as required into the mobile phase to release different batches of sample components from the media.

In all the above embodiments, if an absolute quantitative determination of the sample components is required, each releasing phase should comprise a known amount of calibration material. However, if only relative quantification is required, it may only necessary for each releasing phase to comprise the same amount of calibration material.

DETAILED DESCRIPTION OF EMBODIMENTS OF THE INVENTION

Figure 1:
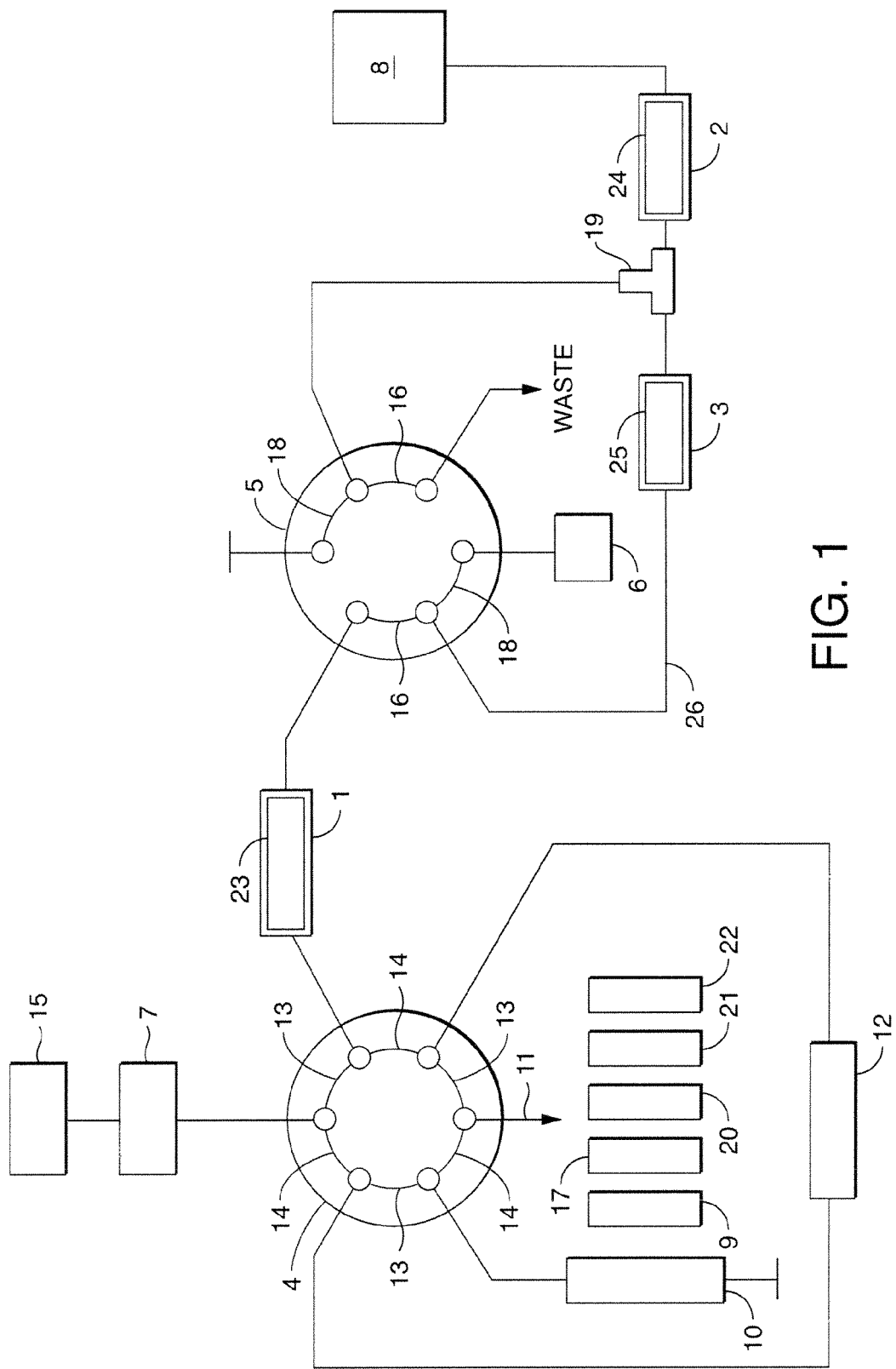
FIG. 1 is a schematic drawing of one embodiment of multidimensional chromatographic apparatus according to one aspect of the invention.

Referring to FIG. 1, an embodiment of a two-dimensional liquid chromatographic apparatus suitable for practicing the invention comprises a first dimension chromatographic column 1 which contains first chromatographic media 23, a second dimension chromatographic column 2 that contains second chromatographic media 24, and a trap column 3 that contains trapping media 25. Two six-port valves 4, 5, a binary liquid chromatograph pump 6, a loading pump 7 and a detector 8 are also provided.

In use, a sample to be analysed is contained in a reservoir 9. With the valve 4 set to the "load" position (wherein its ports are connected as indicated by the lines 13), a syringe or other suction device 10 is used to fill a sample loop 12 by drawing sample from reservoir 9 through a connecting pipe 11. Valve 4 is then turned to the "run" position, wherein its ports are connected as shown by the lines 14. The loading pump 7 is then used to pump a first mobile phase from a reservoir 15 through the sample loop 12 so that the sample present in the sample loop 12 in the flow of first mobile phase to the first dimension chromatographic column 1. During this step, valve 5 may be set so that its ports are connected as indicated by lines 16, which causes the first mobile phase exiting from the column 1 to enter the trap column 3 via the connecting pipe 26, and on leaving the trap column 3 to be discharged to waste via a tee connector 19. (Note that the alternative path for the mobile phase from the tee connector 19 through the second dimension column 2 presents very high impedance, so the vast majority of the flow passes to waste via valve 5).

In an embodiment especially suitable for peptide or protein analysis, the first dimension column 1 may be a SCX (strong cation exchange) column, and the trap column 3 may comprise a short reverse phase column. The first mobile phase (contained in the reservoir 15) is pumped by the loading pump 7 through the valve 4 (set to the "run" position, described above) to the first dimension chromatographic column 1. The first mobile phase may be selected so that at least some components present in a sample previously loaded into the sample loop 12 are retained on the first dimension column 1. Any sample components that are not retained may pass directly to the trap column 3 and may be treated as a batch of sample components, as described below. When the column 1 is an SCX column, the first mobile phase may be a weak solvent that comprises a low concentration of salt.

Means for passing a releasing phase through said first chromatographic separation media, described below, may also be provided. A first batch of sample components may be released from the first dimension column 1 by setting the valve 4 to the "load" position and filling the sample loop 12 with a first releasing phase from a reservoir 17 via the pipe 11. The first releasing phase may comprise a solvent (typically the first mobile phase) and releasing agent, for example a low percentage (typically 10%) of a salt solution. As described in general terms above, the releasing phase may also comprise calibration material. In the case of a sample comprising peptides, the calibration material may comprise one or more peptides that are not retained on the first dimension column in the presence of the releasing phase. The contents of the sample loop 12 may then be introduced into the flow of first mobile phase from the loading pump 7 by setting the valve 4 to the "run" position. The "slug" of releasing phase (comprising the calibration material) present in the sample loop 12 is then carried to the first dimension column 1 where it releases a batch of sample components previously retained thereon. These released sample components (together with the calibration material) then pass to the trap column 3 where they are retained. The first mobile phase and releasing phase (including the salt) continue through the trap column 3, the valve 5 and are discharged to waste, as described above.

A second dimension separation of the components trapped on the trap column 3 may then be carried out by setting valve 5 to the position where its ports are connected as indicated by the lines 18. The binary solvent liquid chromatograph pump 6 may then be used to deliver a second mobile phase to the trap column 3 via the connecting pipe 26. The second mobile phase should be of sufficient strength to release the trapped components and calibration material from the trap column 3 and to carry them through the tee connector 19 to the second dimension column 2. (Note that the other exit of the tee connector 19 is blocked when valve 5 is set so that its ports are connected as indicated by the lines 18, thereby forcing the flow of second mobile phase into the column 2). In the present example, the second dimension column 2 may be a reverse phase analytical column. The pump 6 may be programmed to generate a solvent gradient of gradually increasing strength to effect a chromatographic separation of the sample components released from the trap column 3. The eluent from the second dimension column 2 is passed to a detector 8 which may comprise any suitable chromatographic detector, for example a mass spectrometer, UV absorption detector, refractive index detector, or an evaporative light scattering detector. Conveniently, but not essentially, the trapping media 25 used in trap column 3 and the media 24 used in second dimension column 2 may be similar, so that in effect the separation of the sample components starts on the trap column 3 and continues on the column 2 when the second mobile phase is introduced form the pump 6. However, the trap column 3 is generally very short and of greater capacity (in terms of flow rate) than the second dimension column 2, permitting the first mobile phase and releasing phase to be pumped through it at a higher flow rate than that used for the second dimension separation, particularly when valve 5 is set to discharge the eluent from the trap column 3 to waste. In many practical embodiments, the media 25 used in the trap column 3 will comprise larger particles than those comprised in the media 24 used in the second dimension column 2.

As explained, the calibration material may be chosen so that it is released from the trap column 3 along with the sample components. At least one chromatographic peak corresponding to the calibration material will therefore appear in the second dimension chromatogram, and can be used as a reference to quantitatively determine one or more of the sample components that also produce peaks in the chromatogram.

Once the second dimension separation of the first batch of sample components has been completed, the sample loop 12 may be filled with a different releasing phase (for example, from reservoir 20). This releasing phase may be stronger than the first (for example it may comprise a greater concentration of salt) so that it will release a second batch of sample components from the first dimension column 1, which components have been more strongly bound on the chromatographic media than the first batch. It may also comprise calibration material that is not retained by the first dimension column, typically but not necessarily the same material used in the first releasing phase. On passing through the first dimension column 1 this releasing phase will release the second batch of sample components and carry them, along with the calibration material, to the trap column 3. The pump 6 is then used to supply a second mobile phase via the valve 5 to the trap column 3, thereby releasing the second batch of sample components and the calibration material and passing them to the second dimension column 2. Typically, the mobile phase used will have the same composition of the second mobile phase used to release the first batch of sample components, as described above. The second batch of sample components then undergo separation of the column 2, and the chromatogram produced by detector 8 will comprise at least one peak from the calibration material, allowing quantitative determination of at least one of the second batch of sample components.

Use of the same calibration material, and the same second mobile phase for the first and second batches of sample components in the second dimension calibration results in the chromatographic peak or peaks due to the calibration material occurring in substantially the same place in each chromatogram. This facilitates identification in a complicated chromatogram.

The process may be repeated to release and separate in the second dimension third, fourth, and subsequent batches of sample components, each batch being released from the first dimension column 1 by means of stronger releasing phases, selected from the plurality of reservoirs 21, 22, etc. In the example of the SCX first dimension column, these stronger releasing phases may comprise higher concentrations of salt. Each releasing phase may also comprise calibration material, as discussed.

Operation of a two-dimensional chromatographic system in this way overcomes the problem of many prior methods wherein an internal standard added to a sample usually only elutes along with one or a few of the batches of sample components released from the first dimension column, so that it cannot provide a reference for all the batches. Methods as described also represent an improvement over the alternative prior method wherein samples comprising known amounts of a given sample component are separately analysed to provide a calibration curve, because the calibration material passes through both columns with the same mobile phases and releasing phases as the sample components. This reduces errors due to variation in the chromatographic conditions in the same way as does the use of an internal standard in single dimensional chromatography.

Figure 2:
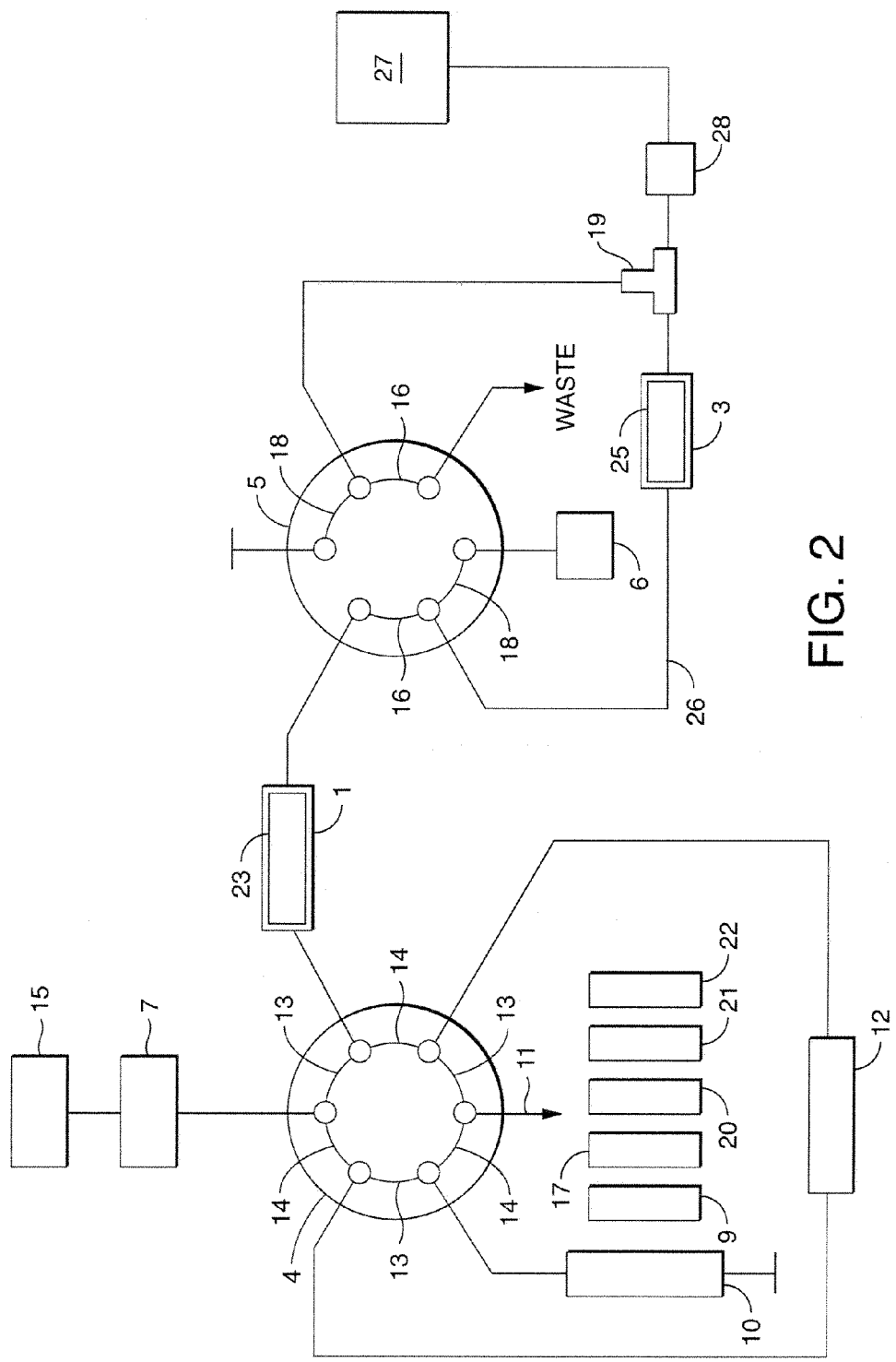
FIG. 2 is a schematic drawing of an embodiment of multidimensional analysis apparatus according to another aspect of the invention.

Referring next to FIG. 2, multidimensional analysis apparatus according to another embodiment of the invention comprises a first dimension chromatographic column 1, a trap column 3 and an analysis device 27. A suitable analysis device 27 may comprise a mass spectrometer. The first dimension column 1 contains first chromatographic media 23 and the trap column 3 contains trapping media 25. Two six-port valves 4, 5, a binary liquid chromatographic pump 6, and a loading pump 7 are also provided. A restrictor 28 is also provided between the tee connector 19 and the analysis device 27.

In use, a sample may be loaded on the column 1 using the valve 4 and its associated components in the same way as described with reference to the FIG. 1 embodiment. During this stage, valve 5 may be set so that the eluent from the trap column 3 is discharged to waste via the tee connector 19. The restrictor 28 ensures that the impedance of path through valve 5 to waste is lower than the impedance into the analysis device 27, so that at least a major portion of the eluent passes to waste rather than to the analysis device.

Batches of sample components may then be released from the trap column 3 using releasing phases from reservoirs 17, 20, 21, etc. as described for the FIG. 1 embodiment. Batches required to be analysed by the analysis device 27 may be admitted into it by setting valve 5 to block the connection from the tee connector 19 to waste, so that the eluent from the trap column 3 (comprising the sample components) passes through the restrictor 28 to the analysis device 27. As in the embodiment described with reference to FIG. 1, each of the releasing phases may comprise calibration material that passes through the first dimension column 1 but is retained, along with the sample components, on the trap column 3. Information produced by the analysis device 27 from the calibration material may then be used as a reference for the quantitative determination of at least some of the sample components present in the batch. Where the analysis device 27 is a mass spectrometer, the calibration material should be chosen so that its mass spectrum comprises one or more mass peaks that are distinct from those produced by the sample components. For example, it may comprise an isotopically labelled variant of one of the sample components.

Figure 3:
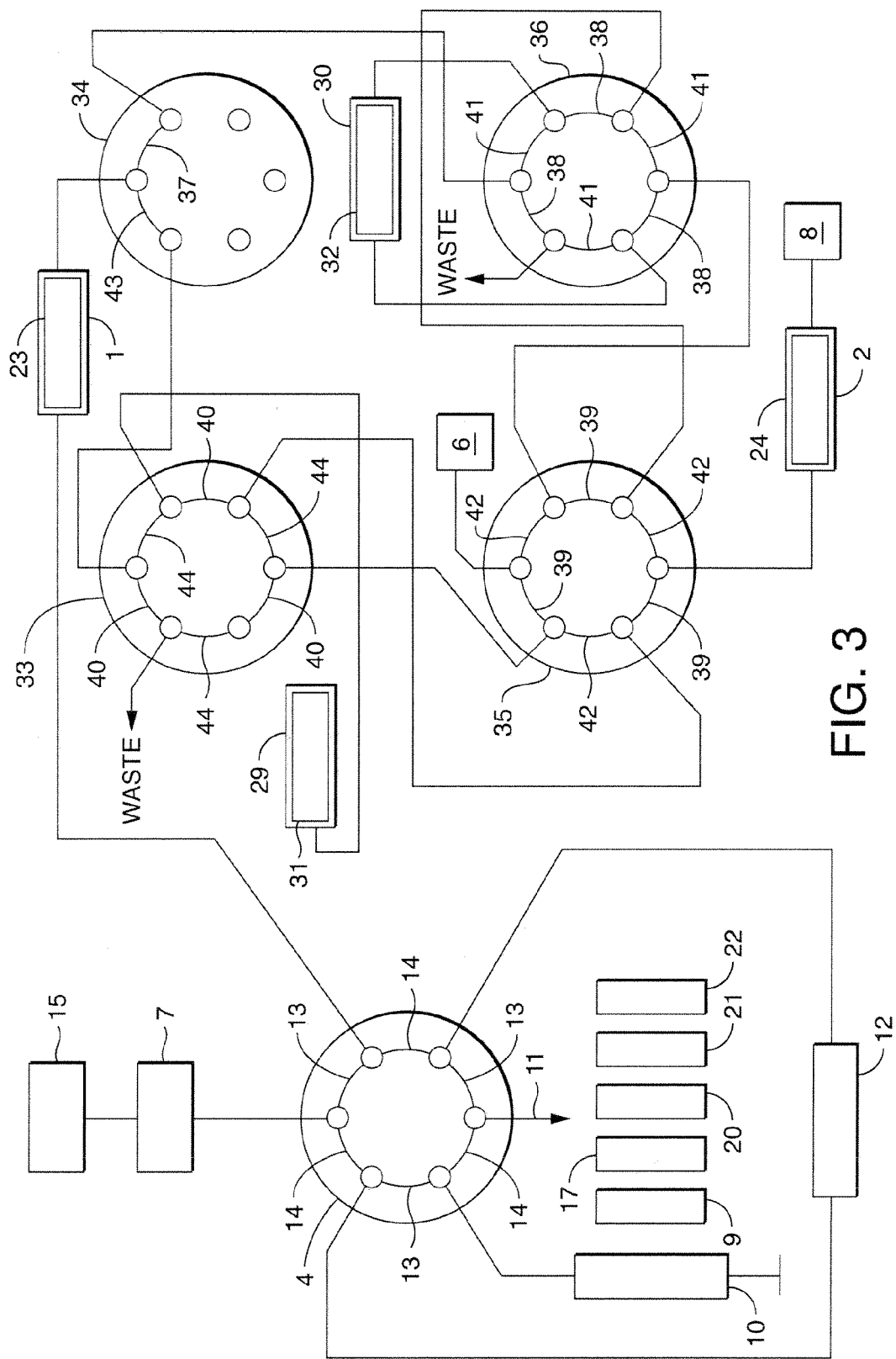
FIG. 3 is a schematic drawing of an embodiment of multidimensional chromatographic apparatus incorporating two trapping columns.

An embodiment of the invention in which two trap columns are provided is shown in FIG. 3. In FIG. 3, reference numerals also present in FIG. 1 relate to apparatus previously descried with reference to FIG. 1. The FIG. 3 embodiment comprises a first dimension column 1 containing first chromatographic media 23, a second dimension column 2 containing second chromatographic media 24, and two trap columns 29, 30 respectively containing trapping media 31 and 32. Five six-port valves 4, 33, 34, 35, and 36, a loading pump 7 and a binary liquid chromatograph pump 6 are also provided.

In use, valves 4, 33, 34, 35 and 36 are initially set to the positions respectively indicated by lines 13, 37, 38, 39 and 40. A sample contained in the sample reservoir 9 is drawn into the sample loop 12 by the syringe 10, as described with reference to the FIG. 1 embodiment. Valve 4 is then changed to the position indicated by the lines 14 and the loading pump 7 used to carry a first mobile phase from the reservoir 15 through the sample loop 12 and, together with the sample, to the first dimension column 1. Eluent from column 1 is passed to waste through valves 34 and 36 (set as indicated by lines 37 and 38, respectively). As in the case of the FIG. 1 embodiment, in a particular example, the chromatographic media 23 in the first dimension column 1 may be SCX media. At least some sample components will be retained on the first dimension column 1.

Valve 36 may then be set to the position indicated by the lines 41 and an aliquot of a first releasing phase from the reservoir 17 may be loaded into the sample loop 12 using the syringe 10, as detailed in respect of loading a sample from the reservoir 9. Valve 4 may then be set to the position indicated by the lines 13 and the loading pump 7 used to carry the releasing phase through the first dimension column 1 through valves 34 and 36 to the trap column 30 and then to waste. The passage of the releasing phase through the first dimension column 1 releases a first batch of sample components that, together with the calibration material comprised in the releasing phase, are retained on the first trap column 30. A second dimension separation of these retained components may then be carried out on the second dimension column 2 using the binary liquid chromatograph pump 6 to deliver a second mobile phase and by setting valves 35 and 36 to the positions indicated by lines 42 and 38 respectively. This results in the second mobile phase passing through the trap column 30 to the column 2 and thence to the detector 8.

While this second dimension separation is being carried out, a second releasing phase (from reservoir 20, for example) may be loaded into the sample loop 12 and passed to the first dimension column 1. Here it may release a second batch of sample components, which may be carried to the second trap column 29 by setting valves 34 and 33 to the positions indicated by lines 43 and 44 respectively. When the second dimension separation of the first batch of sample components is complete, valves 35 and 33 may be set to the positions indicated by lines 39 and 40 respectively, and the pump 6 used to deliver a third mobile phase release sample components from the second trap column 29 and to carry out a second dimension separation of the second batch of sample components on the second dimension column 2. Typically, the third mobile phase may have the same composition as the second mobile phase.

Like the first releasing phase, the second releasing phase may comprise calibration material that will be eluted from the second trap column 29 along with the second batch of sample components and will provide a reference for quantitatively determining at least some of the sample components comprised in the second batch.

It will be seen that the use of the apparatus of FIG. 3 allows simultaneous first and second dimension separations to be carried out. This reduces the time taken to carry out a complete multidimensional analysis. By incorporating calibration material into the releasing phases stored in reservoirs 17, 20, 21, 22, etc, a quantitative calibration of each second dimension separation can be achieved.

Figure 4:
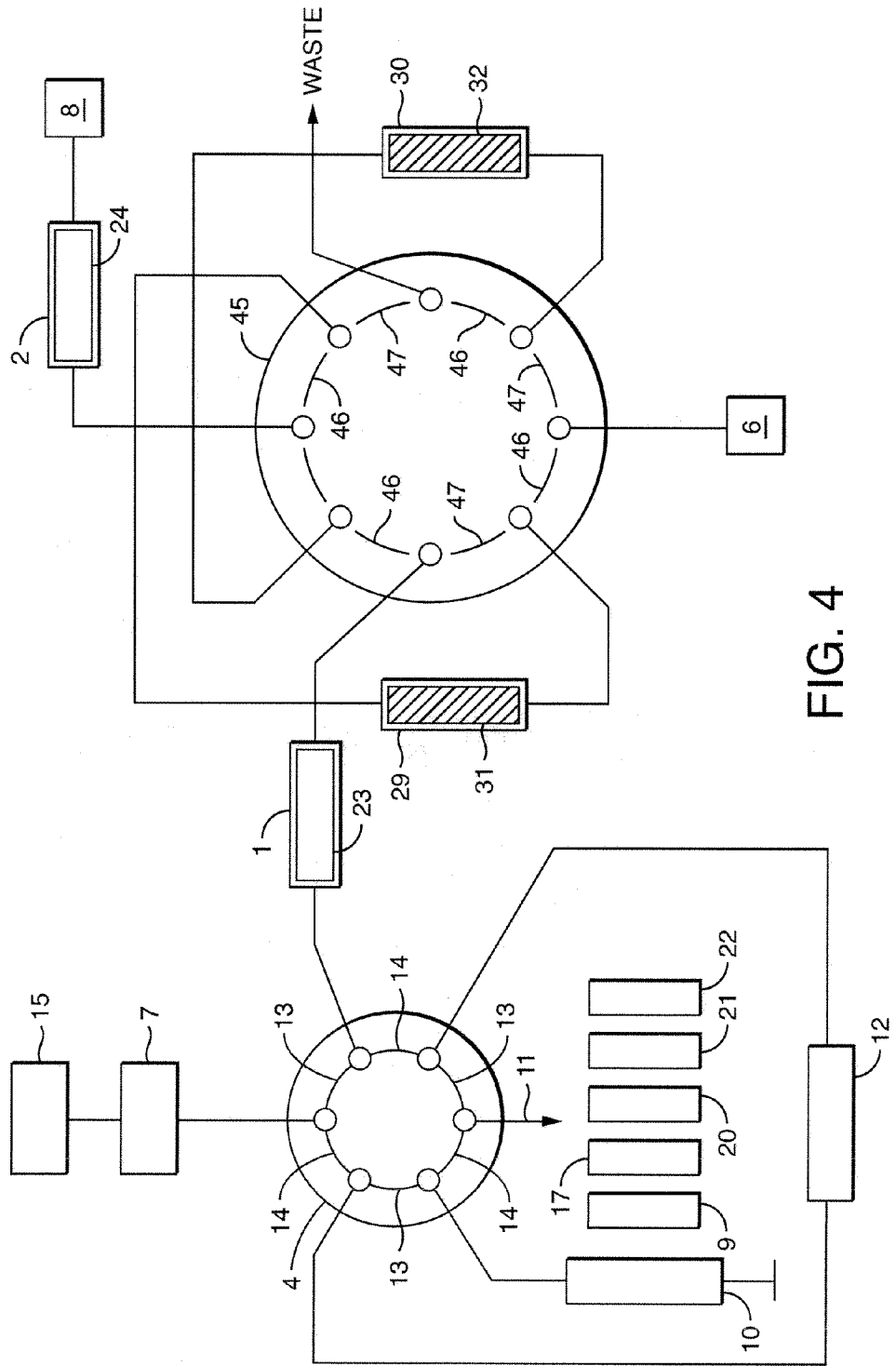
FIG. 4 is a schematic drawing of another embodiment of multidimensional chromatographic apparatus incorporating two trapping columns.

An alternative embodiment of a system incorporating two trap columns is shown in FIG. 4. An eight-port valve 45 is used to direct eluent from the first dimension column 1 to either of two trap columns 29 and 30, and thence to the second dimension column 2 and detector 8. Thus, when valve 45 is in the position such that its ports are connected as indicated by the lines 46, eluent from the first dimension column 1 flows to the first trap column 30 and then to waste, permitting a first batch of sample components to be stored on the trap column 30. Changing valve 45 to the position in which its ports are connected as indicated by the lines 47 allows a second batch of sample components to be stored on the second trap column 29 while the binary liquid chromatograph pump 6 supplies a second mobile phase via the trap column 30 to the second dimension column 2, so that a second dimension separation of the sample components previously stored in the trap column 30 can be carried out. Similarly, a second batch of sample components stored in the trap column 29 can undergo a second dimension separation using a third mobile phase by setting valve 45 to the position in which its ports are connected as indicated by lines 46.

As in the previously described embodiments, releasing phases comprising calibration material are used to transfer batches of sample components from the first dimension column 1 to the two trap columns 29 and 30. The calibration material, which may comprise one or more chemical species, may be selected so that it is not retained of the first dimension column 1 in the presence of the retaining phase, but is retained on the trap column until the second or third mobile phase from pump 6 is introduced to start the second dimension separation. Note that the calibration material does not need to be released immediately on the introduction of the second or third mobile phase. It is required only that it appears at a suitable point in the chromatogram of the second dimension separation, its retention time, like that of the sample components themselves, being determined by the combination of the trap column and the second dimension column.

In particular embodiments, when the first dimension column 1 is an SCX column, the second dimension column 2 and the trap columns 3, 29 and 30, may all comprise reverse phase chromatographic media, and the second and third mobile phases may comprise a solvent gradient of gradually increasing strength, as in many conventional reverse-phase separations. Such a configuration is applicable to the FIGS. 1, 3 and 4 embodiments, and is especially useful for the analysis of complex mixtures of peptides and proteins. However, it will be appreciated that the methods and apparatus of the invention can equally well be applied with many other combinations of multidimensional analysis techniques, for example where both the first and second dimension columns are reverse phase columns on which different separations are carried out as a result of the use of different mobile phases and releasing phases, or combinations of normal-phase and reverse phase columns. Similarly, it is within the scope of the invention to use a capillary electrophoretic separation for at least one of separation dimensions, or other chromatographic techniques such as size exclusion chromatography or gel permeation chromatography.

In general terms the invention may be used with many other types of multidimensional analysis apparatus, particularly those in which sample components are temporarily stored between the first and second dimension separations. By incorporating calibration material in the releasing phases used to carry sample components from the trap to the second dimension analysis stage, the presence of calibration material in each batch of sample components undergoing a second dimension separation or analysis can be ensured. Use of the invention therefore overcomes the difficulty of quantitative calibration encountered in prior multidimensional analytical techniques wherein an internal standard added to a sample appears in only one or a few of the batches of sample components sent for second dimension analysis.

The invention claimed is:

1. A method of chromatography comprising the following steps:
   a) introducing a sample comprising one or more sample components into a first mobile phase, and passing the resulting fluid through first chromatographic separation media so that at least some of the sample components are retained on said first chromatographic separation media;
   b) passing a releasing phase comprising a calibration material through said first chromatographic separation media to release therefrom at least some of the retained sample components into said releasing phase, wherein said calibration material is selected such that it is not retained on the first chromatographic separation media;
   c) passing said releasing phase through a second chromatographic separation media that is capable of separating at least some of the released sample components and said calibration material; and
   d) passing eluent from said second chromatographic separation media into detector means.

2. A method of chromatography as claimed in claim 1 wherein one or more further batches of sample components are released from said first chromatographic separation media and passed to said second chromatographic separation media by passing one or more further releasing phases into said first chromatographic separation media after the previously released batch of sample components have been passed to said second chromatographic separation media, each said one or more further releasing phases comprising a calibration material.

3. A method of chromatography as claimed in claim 1 wherein after said sample components have been passed into said second chromatographic separation media in said releasing phase, a modifying phase is passed into said second chromatographic separation media to generate a second mobile phase.

4. A method of chromatography as claimed in claim 3 wherein said releasing phase is discontinued after said modifying phase has passed into said second chromatographic separation media.

5. A method of chromatography comprising the following steps:
   a) introducing a sample comprising one or more sample components into a first mobile phase, and passing the resulting fluid through first chromatographic separation media so that at least some of the sample components are retained on said first chromatographic separation media;
   b) passing a releasing phase comprising a calibration material through said first chromatographic separation media to release therefrom at least some of the retained sample components into said releasing phase, wherein said calibration material is selected such that it is not retained on the first chromatographic separation media;
   c) passing said releasing phase into trapping media capable of trapping at least some of the released sample components and said calibration material; and
   d) passing a second mobile phase through said trapping media into an analysis device.

6. A method of chromatography as claimed in claim 5 wherein said analysis device comprises second chromatographic separation media capable of separating at least some of said sample components and said calibration material, and wherein eluent from said second chromatographic separation means is passed into detector means.

7. A method as claimed in claim 5 wherein said second mobile phase is capable of releasing at least some sample components from said trapping media.

8. A method of chromatography as claimed in claim 5 wherein one or more further batches of sample components are released from said first chromatographic media and passed to said trapping media by passing one or more further releasing phases into said first chromatographic separation media after the previously released batch of sample components have been passed to said analysis device, each said one or more further releasing phase comprising calibration material.

9. A method of chromatography as claimed in claim 8 wherein said analysis device comprises second chromatographic separation media capable of separating at least some of said sample components and said calibration material, and wherein eluent from said second chromatographic separation means is passed into detector means.

10. A method of chromatography as claimed in claim 5 wherein said first mobile phase is discharged to waste after passing through said trapping media.

11. A method of chromatography as claimed in claim 5 wherein said calibration material is capable of being trapped on the trapping media along with said at least some sample components.

12. A method of chromatography as claimed in claim 11 wherein said calibration material is further selected so that it may be released from said trapping media by said second mobile phase.

13. A method of chromatography comprising the following steps:
   a) introducing a sample comprising one or more sample components into a first mobile phase comprising a calibration material, and passing the resulting fluid through said first chromatographic separation media so that at least some of the sample components are separated from one another on said first chromatographic separation media, wherein said calibration material is selected such that it is not retained on the first chromatographic separation media;

b) passing at least some of said first mobile phase into trapping media capable of trapping at least some of said sample components and said calibration material; and c) passing a second mobile phase through said trapping media into an analysis device, said second mobile phase being capable of releasing from said trapping media said calibration material and at least some of said sample components trapped thereon.

14. A method of chromatography as claimed in claim 13 wherein only certain ones of said sample components eluting in said first mobile phase from said first chromatographic separation media are passed to said trapping means, while others of said sample components are discharged to waste.

15. A method of chromatography as claimed in claim 14 wherein said analysis device comprises second chromatographic separation media capable of separating at least some of said sample components and said calibration material, and wherein eluent from said second chromatographic separation means is passed into detector means.

16. A method of chromatography as claimed in claim 14 wherein groups of sample components eluting from the first chromatographic separation media are separately trapped on said trapping media, and subsequently released by said second mobile phase and pass into said second chromatographic separation media to undergo further separation.

17. A method of chromatography as claimed in claim 13 wherein an aliquot of said calibration material is introduced into said second mobile phase, and wherein the composition of said second mobile phase varies with time and is initially such that said calibration material is retained on said trapping media, but is later such that said calibration material is released from said trapping media.

18. Chromatographic apparatus comprising:
  a) means for introducing an aliquot of a sample comprising one or more sample components into a flow of a first mobile phase;
  b) first chromatographic separation media disposed to receive said flow of a first mobile phase, said first chromatographic separation media capable of retaining at least some of said sample components in the presence of said first mobile phase;
  c) means for passing a releasing phase comprising a calibration material through said first chromatographic separation media to release therefrom at least some of the retained sample components into said releasing phase, wherein said calibration material is selected such that it is not retained on the first chromatographic separation media;
  d) second chromatographic separation media that is capable of separating at least some of the released sample components and said calibration material, disposed to receive at least some of the eluent from said first chromatographic separation media while said releasing phase is being passed into it; and
  e) detector means disposed to receive eluent from said second chromatographic separation media.

19. Chromatographic apparatus comprising:
  a) means for introducing an aliquot of a sample comprising one or more sample components into a flow of a first mobile phase;
  b) first chromatographic separation media disposed to receive said flow of a first mobile phase, said first chromatographic separation media capable of retaining at least some of said sample components in the presence of said first mobile phase;
  c) trapping media disposed to receive at least some eluent from said first chromatographic separation media;
  d) means for passing a releasing phase comprising a calibration material through said first chromatographic separation media to release therefrom at least some of the retained sample components into said releasing phase, wherein said calibration material is selected such that it is not retained on the first chromatographic separation media, and passing said releasing phase into said trapping media such that said calibration material and at least some of the released sample components are retained on said trapping media;
  e) an analysis device disposed to receive eluent from said trapping media; and
  f) means for passing a second mobile phase through said trapping media to release therefrom at least some of the trapped sample components and calibration material so that they pass to said analysis device.

20. Chromatographic apparatus as claimed in claim 19 wherein said analysis device is capable of producing quantitative information for at least one of said sample components relative to said calibration material.

21. Chromatographic apparatus as claimed in claim 20 wherein said analysis device comprises second chromatographic separation media and a detector disposed to receive at least some of the eluent from said second chromatographic separation media.

22. Chromatographic apparatus as claimed in claim 21 further comprising means for directing to waste said first mobile phase after it has passed through said trapping media.

23. Chromatographic apparatus as claimed in claim 21 wherein said means for introducing a second mobile phase comprises a liquid chromatographic pump capable of generating a solvent gradient.

24. Chromatographic apparatus as claimed in claim 21 wherein said means for introducing an aliquot of a sample comprises a loading pump for generating said flow of a first mobile phase, a sample valve and a sample loop, said loading pump, sample valve and sample loop being configured so that an aliquot of a said sample introduced into said sample loop may be carried to said first chromatographic separation media in said flow of a first mobile phase.

25. Chromatographic apparatus as claimed in claim 24 further comprising means for introducing through said sample valve into said sample loop aliquots of a said sample or a said releasing phase comprising calibration material from any of a plurality of reservoirs.

26. Chromatographic apparatus as claimed in claim 25 wherein at least one of said reservoirs is provided with a releasing phase comprising calibration material and a releasing agent having a predetermined concentration and at least one other of said reservoirs is provided with a calibration material and a releasing agent having a concentration differing from said predetermined concentration.

27. Chromatographic apparatus as claimed in claim 26 wherein said first chromatographic separation media comprises strong cation exchange media, said releasing agent comprises a salt solution, and said trapping media and said second chromatographic separation media both comprise reverse-phase chromatographic separation media.

28. Chromatographic apparatus as claimed in claim 24 wherein said first chromatographic separation media comprises ion-pairing chromatographic separation media and both said trapping media and said second chromatographic separation media comprise reverse-phase chromatographic separation media.

29. Chromatographic apparatus as claimed in claim 24 wherein said first chromatographic separation media, said trapping media and second chromatographic separation media all comprise reverse-phase chromatographic separation media.

30. Chromatographic apparatus as claimed in claim 20 wherein said analysis device comprises a mass spectrometer.

31. Chromatographic apparatus as claimed in claim 21 wherein said detector comprises a mass spectrometer.

32. A method of chromatography comprising the following steps:
   a) introducing a sample comprising one or more sample components into a first mobile phase, and passing the resulting fluid through first chromatographic separation media so that at least some of the sample components are retained on said first chromatographic separation media;
   b) passing a first releasing phase comprising a calibration material into said first chromatographic separation media to release therefrom a first batch of the retained sample components into said first releasing phase;
   c) passing said first releasing phase into first trapping media capable of trapping at least some of the released sample components and said calibration material;
   d) passing a second mobile phase through said first trapping media into an analysis device;
   e) after step c) has been completed, passing a second releasing phase comprising a calibration material into said first chromatographic separation media to release therefrom a second batch of the retained sample components into said second releasing phase;
   f) passing said second releasing phase into second trapping media capable of trapping at least some of the released sample components and said calibration material; and
   g) passing a third mobile phase through said second trapping media into said analysis device;
   wherein said calibration material in each of said first and second releasing phases is selected such that it is not retained on the first chromatographic separation media.

33. A method of chromatography as claimed in claim 32 wherein said analysis device comprises second chromatographic separation media capable of separating at least some of said sample components and said calibration material, and wherein eluent from said second chromatographic separation means is passed into detector means.

34. Chromatographic apparatus comprising:
   a) means for introducing an aliquot of a sample comprising one or more sample components into a flow of a first mobile phase;
   b) first chromatographic separation media disposed to receive said flow of a first mobile phase and capable of retaining at least some of said sample components in the presence of said first mobile phase;
   c) first and second trapping media arranged so that either may receive eluent from said first chromatographic separation media as required;
   d) means for passing a first releasing phase comprising a calibration material through said first chromatographic separation media to release therefrom a first batch of the retained sample components into said first releasing phase;
   e) means for passing said first releasing phase into said first trapping media capable of trapping at least some of the released sample components and said calibration material;
   f) means for passing a second releasing phase comprising a calibration material through said first chromatographic separation media to release therefrom a second batch of the retained sample components into said second releasing phase;
   g) means for passing said second releasing phase into said second trapping media capable of trapping at least some of the released sample components and said calibration material;
   h) an analysis device capable of receiving eluent from either said first or said second trapping media as required;
   i) means for passing a second mobile phase through said first trapping media to release therefrom at least some of the trapped sample components and calibration material and to pass them to said analysis device; and
   j) means for passing a third mobile phase through said second trapping media to release therefrom at least some of the trapped sample components and calibration material and to pass them to said analysis device;
   wherein said calibration material in each of said first and second releasing phases is selected such that it is not retained on the first chromatographic separation media.

35. Chromatographic apparatus as claimed in claim 34 wherein said analysis device comprises second chromatographic separation media capable of separating at least some of said sample components and said calibration material, and wherein eluent from said second chromatographic separation means is passed into detector means.

\* \* \* \* \*